United States Patent
Linsell

(10) Patent No.: US 6,831,150 B2
(45) Date of Patent: Dec. 14, 2004

(54) REDUCTIVE ALKYLATION PROCESS

(75) Inventor: Martin S. Linsell, San Mateo, CA (US)

(73) Assignee: Theravance, Inc., South San Francisco, CA (US)

( * ) Notice: Subject to any disclaimer, the term of this patent is extended or adjusted under 35 U.S.C. 154(b) by 454 days.

(21) Appl. No.: 09/847,060

(22) Filed: May 1, 2001

(65) Prior Publication Data

US 2002/0010131 A1 Jan. 24, 2002

Related U.S. Application Data

(60) Provisional application No. 60/201,178, filed on May 2, 2000, and provisional application No. 60/213,148, filed on Jun. 22, 2000.

(51) Int. Cl.[7] ............................................. A61K 38/00
(52) U.S. Cl. ...................... 530/322; 530/317; 530/333; 530/345; 514/8; 514/9
(58) Field of Search ............................... 530/322, 317, 530/333, 345; 514/8, 9

(56) References Cited

U.S. PATENT DOCUMENTS

| | | | |
|---|---|---|---|
| 4,643,987 A | 2/1987 | Nagarajan et al. | 514/8 |
| 4,698,327 A | 10/1987 | Nagarajan et al. | 514/8 |
| 5,591,714 A | 1/1997 | Nagarajan et al. | 514/9 |
| 5,750,509 A | 5/1998 | Malabarba et al. | 514/11 |
| 5,840,684 A | 11/1998 | Cooper et al. | 514/11 |
| 5,916,873 A | 6/1999 | Cooper et al. | 514/9 |
| 5,952,466 A | 9/1999 | Berglund et al. | 530/345 |
| 5,998,581 A | 12/1999 | Berglund et al. | 530/345 |
| 6,620,781 B2 * | 9/2003 | Linsell | 514/8 |

FOREIGN PATENT DOCUMENTS

| | | | |
|---|---|---|---|
| EP | 0201251 | 12/1986 | C07K/9/00 |
| EP | 0667353 | 8/1995 | C07K/9/00 |
| EP | 0816378 | 1/1998 | C07K/9/00 |
| EP | 0873997 | 10/1998 | C07K/9/00 |
| WO | 98/21952 | 5/1998 | A01N/37/18 |
| WO | 99/42476 | 8/1999 | C07K/7/50 |
| WO | 00/39156 | 7/2000 | C07K/9/00 |
| WO | 00/59528 | 10/2000 | A61K/38/08 |

OTHER PUBLICATIONS

Cooper, R.D., et al., "Reductive Alkylation of Glycopeptide Antibiotics: Synthesis and Antibacterial Activity", *The Journal of Antibiotics*, 49 (6), pp. 575–581, (Jun. 1996).

Nagarajan, R., et al., "Synthesis and Antibacterial Evaluation of N–Alkyl Vancomycins", *The Journal of Antibiotics*, XLII (1), pp. 63–72, (Jan. 1989).

Nicolaou, K.C., et al., "Chemistry, Biology, and Medicine of the Glycopeptide Antibiotics", *Angew. Chem. Int. Ed.*, 38, pp. 2097–2152, (1999).

Pavlov, A.Y., et al., "Chemical Modification of Glycopeptide of Glycopeptide Antibiotics [VC1]", *Russian Journal Of Bioorganic Chemistry*, 24 (9), pp. 570–587, (1998).

Rodriguez, M.J., et al., "Novel Glycopeptide Antibiotics: N–Alkylated Derivatives Active Against Vancomycin–Resistant Enterococci", *The Journal of Antibiotics*, 51 (6), pp. 560–569, (Jun. 1998).

Snyder, N.J., et al., "Enzymatic Deacylation of Teicoplanin Followed by Redictive Alkylation: Synthesis and Antibacterial Activity of New Glycopeptides", *The Journal of Antibiotics*, 51 (10), pp. 945–951, (Oct. 1998).

* cited by examiner

*Primary Examiner*—Karen Cochrane Carlson
*Assistant Examiner*—Anand U Desai
(74) *Attorney, Agent, or Firm*—Jeffrey A. Hagenah; David E. Boone

(57) ABSTRACT

The invention provides a novel reductive alkylation method useful for selectively alkylating saccharide-amines of glycopeptide antibiotics.

34 Claims, No Drawings

REDUCTIVE ALKYLATION PROCESS

PRIORITY OF INVENTION

This application claims priority to U.S. Provisional Application No. 60/201,178, filed May 2, 2000; and to U.S. Provisional Application No. 60/213,148, filed Jun. 22, 2000, which applications are incorporated herein by reference in their entirety.

BACKGROUND OF THE INVENTION

1. Field of the Invention

This invention is directed to an improved method for reductively alkylating a saccharide-amine of a glycopeptide antibiotic. Specifically, the method of the invention allows for selective alkylation at a saccharide-amine over other amine sites in the glycopeptide (e.g. a leucinyl nitrogen).

2. Background

Glycopeptides are a well-known class of antibiotics produced by various microorganisms (see *Glycopeptide Antibiotics,* edited by R. Nagarajan, Marcel Dekker, Inc. New York (1994)). These complex multi-ring peptide compounds are effective antibacterial agents against a majority of Gram-positive bacteria. Although potent antibacterial agents, the glycopeptides antibiotics are not used in the treatment of bacterial diseases as often as other classes of antibiotics, such as the semi-synthetic penicillins, cephalosporins and lincomycins, due to concerns regarding toxicity.

In recent years, however, bacterial resistance to many of the commonly-used antibiotics has developed (see J. E. Geraci et al., *Mayo Clin. Proc.* 1983, 58, 88–91; and M. Foldes, *J. Antimicrob. Chemother.* 1983, 11, 21–26). Since glycopeptide antibiotics are often effective against these resistant strains of bacteria, glycopeptides such as vancomycin have become the drugs of last resort for treating infections caused by these organisms. Recently, however, resistance to vancomycin has appeared in various microorganisms, such as vancomycin-resistant enterococci (VRE), leading to increasing concerns about the ability to effectively treat bacterial infections in the future (see Hospital Infection Control Practices Advisory Committee, *Infection Control Hospital Epidemiology,* 1995, 17, 364–369; A. P. Johnson et al., *Clinical Microbiology Rev.,* 1990, 3, 280–291; G. M. Eliopoulos, *European J. Clinical Microbiol., Infection Disease,* 1993, 12, 409–412; and P. Courvalin, *Antimicrob. Agents Chemother,* 1990, 34, 2291–2296).

In an attempt to identify agents with improved antibacterial properties, or to identify agents that are effective against resistant bacterial strains, numerous derivatives of vancomycin and other glycopeptides have been prepared. For example, see U.S. Pat. Nos. 4,639,433; 4,643,987; 4,497,802; 5,840,684; and 5,843,889. Other derivatives are disclosed in EP 0 802 199; EP 0 801 075; WO 97/28812; WO 97/38702; WO 98/52589; WO 98/52592; and in *J. Amer. Chem. Soc.,* 1996, 118, 13107–13108; *J. Amer. Chem. Soc.,* 1997, 119, 12041–12047; and *J. Amer. Chem. Soc.,* 1994, 116, 4573–4590.

One group of glycopeptide derivatives that has been reported to have useful antibiotic properties includes glycopeptide compounds that are alkylated at a nitrogen on a saccharide of the glycopeptide. See for example, U.S. Pat. Nos. 5,919,756; 5,843,889; 5,916,873; 4,698,327; and 5,591,714; and European Patent Application Publication Nos. EP 435 503A1; and EP 667 353A1. One difficulty that is encountered in preparing such alkylated derivatives is the non-selective alkylation at multiple amine sights within the glycopeptide compound. For example, vancomycin has a vancosamine amino group, and a leucinyl amino group. Thus, alkylation under standard conditions typically provides a mixture of mono- and di-alkylated compounds.

U.S. Pat. Nos. 5,952,466 and 5,998,581 disclose a method for the reductive alkylation of a copper complex of a glycopeptide antibiotic such as vancomycin or A82846B, which favors alkylation at the saccharide amino group. In spite of this disclosure, there is currently a need for additional methods that are useful for the selective alkylation of glycopeptide antibiotics at a saccharide-amino group. In particular, there is a need for highly selective methods that are simple and efficient to carry out.

SUMMARY OF THE INVENTION

Previously, the reductive alkylation of glycopeptide antibiotics was carried out by combining an aldehyde, a glycopeptide antibiotic, and a suitable base to form an imine and/or hemiaminal; subsequently adding a suitable reducing agent (e.g. sodium cyanoborohydride); and then adding a suitable acid (e.g. trifluoroacetic acid).

Applicant has unexpectedly discovered that by contacting the glycopeptide and the aldehyde to form the imine and/or hemiaminal in the presence of a suitable base, and then acidifying the mixture before contact with the reducing agent, the selectivity for the reductive alkylation at a saccharide-amine is significantly improved, i.e. reductive alkylation at a saccharide-amino group (e.g. a vancosamine amino group) in vancomycin is favored over reductive alkylation at other amino groups (e.g. a leucinyl amino group) in vancomycin.

Accordingly, the present invention provides a method for alkylating a glycopeptide that comprises a saccharide-amine comprising:

combining an aldehyde or ketone, a suitable base, and the glycopeptide or a salt thereof, to provide a reaction mixture;

acidifying the reaction mixture; and combining the reaction mixture with a suitable reducing agent, to provide a glycopeptide that is alkylated at the saccharide-amine.

Preferably, the glycopeptide comprises at least one amino group other than the saccharide-amine. More preferably, the glycopeptide is vancomycin or A82846B.

Preferably, the reductive alkylation at the saccharide-amine is favored over reductive alkylation at another amino group of the glycopeptide by at least about 10:1; and more preferably, by at least about 15:1 or about 20:1.

The reductive alkylation is typically carried out in the presence of a suitable solvent or combination of solvents, such as, for example, a halogenated hydrocarbon (e.g. methylene chloride), a linear or branched ether (e.g. diethyl ether, tetrahydrofuran), an aromatic hydrocarbon (e.g. benzene or toluene), an alcohol (methanol, ethanol, or isopropanol), dimethylsulfoxide (DMSO), N,N-dimethylformamide, acetonitrile, water, 1,3-dimethyl-3,4,5, 6-tetrahydro-2(1H)-pyrimidone, tetramethyl urea, N,N-dimethylacetamide, diethylformamide (DMF), 1-methyl-2-pyrrolidinone, tetramethylenesulfoxide, glycerol, ethyl acetate, isopropyl acetate, N,N-dimethylpropylene urea (DMPU) or dioxane. Preferably the alkylation is carried out in acetonitrile/water, or DMF/methanol.

Preferably the reduction (i.e. treatment with the reducing agent) is carried out in the presence of a protic solvent, such as, for example, an alcohol (e.g. methanol, ethanol, propanol, isopropanol, or butanol), water, or the like.

The reductive alkylation can be carried out at any suitable temperature from the freezing point to the reflux temperature of the reaction mixture. Preferably the reaction is carried out at a temperature in the range of about 0° C. to about 100° C. More preferably at a temperature in a range of about 0° C. to about 50° C., or in a range of about 20° C. to about 30° C.

Any suitable base can be employed in the reductive alkylation. Preferred bases include tertiary amines (e.g. diisopropylethylamine, N-methylmorpholine or triethylamine) and the like.

Any suitable acid can be used to acidify the reaction mixture. Suitable acids include carboxylic acids (e.g. acetic acid, trichloroacetic acid, citric acid, formic acid, or trifluoroacetic acid), mineral acids (e.g. hydrochloric acid, sulfuric acid, or phosphoric acid), and the like. A preferred acid is trifluoroacetic acid.

Suitable reducing agents for carrying out reductive alkylations are known in the art. Any suitable reducing agent can be employed in the methods of the invention, provided it is compatible with the functionality present in the glycopeptide. For example, suitable reducing agents include sodium cyanoborohydride, sodium triacetoxyborohydride, pyridine/borane, sodium borohydride, and zinc borohydride. The reduction can also be carried out in the presence of a transition metal catalyst (e.g. palladium or platinum) in the presence of a hydrogen source (e.g. hydrogen gas or cycloheadiene). See for example, *Advanced Organic Chemistry*, Fourth Edition, John Wiley & Sons, New York (1992), 899–900.

Upon completion of the reductive alkylation, the alkylated glycopeptide can be isolated from the reaction mixture using standard techniques. For example, the alkylated glycopeptide can be precipitated from the reaction mixture with acetonitrile, or the reaction mixture can be poured into water, and sodium bicarbonate can be added to a pH of about 5 to provide the alkylated glycopeptide as a precipitate.

Any glycopeptide comprising an amino saccharide can be employed in the methods of the invention. Such glycopeptides are well-known in the art and are either commercially available or may be isolated using conventional procedures. For example, suitable glycopeptides are disclosed in, and can be prepared from, glycopeptides disclosed in, U.S. Pat. Nos. 3,067,099; 3,338,786; 3,803,306; 3,928,571; 3,952,095; 4,029,769; 4,051,237; 4,064,233; 4,122,168; 4,239,751; 4,303,646; 4,322,343; 4,378,348; 4,497,802; 4,504,467; 4,542,018; 4,547,488; 4,548,925; 4,548,974; 4,552,701; 4,558,008; 4,639,433; 4,643,987; 4,661,470; 4,694,069; 4,698,327; 4,782,042; 4,914,187; 4,935,238; 4,946,941; 4,994,555; 4,996,148; 5,187,082; 5,192,742; 5,312,738; 5,451,570; 5,591,714; 5,721,208; 5,750,509; 5,840,684; and 5,843,889. Preferably, the glycopeptide is vancomycin or A82846B.

Preferably, the present invention provides a method for preparing an alkylated glycopeptide comprising: combining an aldehyde or ketone, a suitable base, and a compound of formula I:

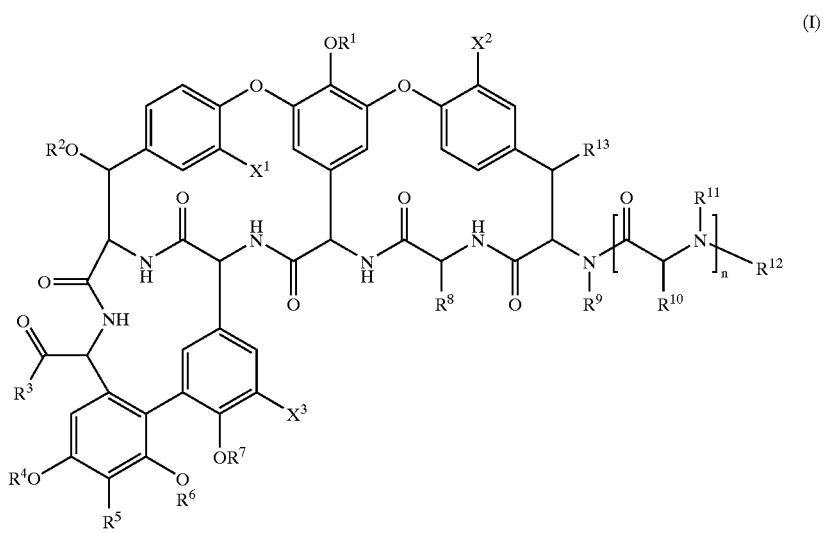

wherein:
$R^1$ is an amino saccharide group;
$R^2$ is hydrogen or a saccharide group;
$R^3$ is —$OR^e$, —$NR^cR^c$, —O—$R^a$—Y—$R^b$—$(Z)_x$, —$NR^c$—$R^a$—Y—$R^b$—$(Z)_x$, —$NR^cR^e$, or —O—$R^e$;
$R^4$ is selected from the group consisting of hydrogen, alkyl, substituted alkyl, alkenyl, substituted alkenyl, alkynyl, substituted alkynyl, —$C(O)R^d$ and a saccharide group;
$R^5$ is selected from the group consisting of hydrogen, halo, —$CH(R^c)$—$NR^cR^c$, —$CH(R^c)$—$NR^cR^e$, —$CH(R^c)$—$NR^c$—$R^a$—Y—$R^b$—$(Z)_x$, —$CH(R^c)$—$R^x$, and —$CH(R^c)$—$NR^c$—$R^a$—$C(=O)$—$R^x$;
$R^6$ is selected from the group consisting of hydrogen, alkyl, substituted alkyl, alkenyl, substituted alkenyl, alkynyl, substituted alkynyl, —$C(O)R^d$ and a saccharide group;
$R^7$ is selected from the group consisting of hydrogen, alkyl, substituted alkyl, alkenyl, substituted alkenyl, alkynyl, substituted alkynyl, and —$C(O)R^d$;
$R^8$ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R⁹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R¹⁰ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or R⁸ and R¹⁰ are joined to form —Ar¹—O—Ar²—, where Ar¹ and Ar² are independently arylene or heteroarylene;

R¹¹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or R¹⁰ and R¹¹ are joined, together with the carbon and nitrogen atoms to which they are attached, to form a heterocyclic ring;

R¹² is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)R$^d$, —C(NH)R$^d$, —C(O)NR$^c$R$^c$, —C(O)OR$^d$, and —C(NH)NR$^c$R$^c$, or R¹¹ and R¹² are joined, together with the nitrogen atom to which they are attached, to form a heterocyclic ring;

R¹³ is selected from the group consisting of hydrogen or —OR¹⁴;

R¹⁴ is selected from hydrogen, —C(O)R$^d$ and a saccharide group;

each R$^a$ is independently selected from the group consisting of alkylene, substituted alkylene, alkenylene, substituted alkenylene, alkynylene and substituted alkynylene;

each R$^b$ is independently selected from the group consisting of a covalent bond, alkylene, substituted alkylene, alkenylene, substituted alkenylene, alkynylene and substituted alkynylene (in one preferred embodiment, R$^b$ is not a covalent bond when Z is hydrogen);

each R$^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;

each R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;

R$^e$ is a saccharide group;

R$^x$ is a nitrogen-linked amino saccharide or a nitrogen-linked heterocycle;

X¹, X² and X³ are independently selected from hydrogen or chloro;

each Y is independently selected from the group consisting of oxygen, sulfur, —S—S—, —NR$^c$—, —S(O)—, —SO₂—, —NR$^c$C(O)—, —OSO₂—, —OC(O)—, —NR$^c$SO₂—, —C(O)NR$^c$—, —C(O)O—, —SO₂NR$^c$—, —SO₂O—, —P(O)(OR$^c$)O—, —P(O)(OR$^c$)NR$^c$—, —OP(O)(OR$^c$)O—, —OP(O)(OR$^c$)NR$^c$—, —OC(O)O—, —NR$^c$C(O)O—, —NR$^c$C(O)NR$^c$—, —OC(O)NR$^c$—, —C(=O)—, and —NR$^c$SO₂NR$^c$—;

each Z is independently selected from hydrogen, aryl, cycloalkyl, cycloalkenyl, heteroaryl and heterocyclic;

n is 0, 1 or 2; and x is 1 or 2;

or a stereoisomer thereof; to provide a reaction mixture;

acidifying the reaction mixture; and combining the reaction mixture with a suitable reducing agent, to provide the corresponding glycopeptide alkylated at the amino group of the amino saccharide.

Preferably, R¹ is an amino saccharide of formula (III):

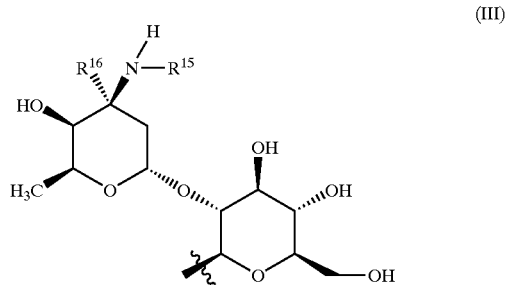

(III)

wherein R¹⁵ is H; and R¹⁶ is hydrogen or methyl.

Preferably, R² is hydrogen.

Preferably, R³ is —OR$^c$ or —NR$^c$R$^c$; more preferably R³ is —OH.

Preferably, R³ is —OH; —NH—(CH₂)₃—N(CH₃)₂; N—(D-glucosamine); —NHCH(CO₂CH₃)CH₂CO₂CH₃; —NH(CH₂)₃-(morpholin-4-yl); —NH(CH₂)₃—NH(CH₂)₂CH₃; —NH(CH₂-piperidin-1-yl; —NH(CH₂)₄NHC(N)NH₂; —NH(CH₂)₂—N⁺(CH₃)₃; —NHCH(COOH)(CH₂)₃NHC(N)NH₂; —NH—[(CH₂)₃—NH—]₃—H; —N[(CH₂)₃N(CH₃)₂]₂; —NH(CH₂)₃-imidazol-1-yl; —NHCH₂-4-pyridyl; —NH(CH₂)₃CH₃; —NH(CH₂)₂OH; —NH(CH₂)₅OH; —NH(CH₂)₂OCH₃; —NHCH₂-tetrahydrofuran-2-yl; —N[(CH₂)₂OH]₂; —NH(CH₂)₂N[(CH₂)₂OH]₂; —NHCH₂COOH; —NHCH(COOH)CH₂OH; —NH(CH₂)₂COOH; N-(glucamine); —NH(CH₂)₂COOH; —NH(CH₂)₃SO₃H; —NHCH(COOH)(CH₂)₂NH₂; —NHCH(COOH)(CH₂)₃NH₂; —NHCH(COOH)CH₂CO₂(CH₂)₃—N⁺(CH₃)₃; —NHCH(COOH)CH₂CO₂(CH₂)₂C(O)—N(CH₃)₂; —NHCH(COOH)CH₂CO₂(CH₂)₃-morpholin-4-yl; —NHCH(COOH)CH₂CO₂(CH₂)₂OC(O)C(CH₃)₃; —NHCH(CH₂COOH)CO₂(CH₂)₃—N⁺(CH₃)₃; —NHCH(CH₂COOH)CO₂(CH₂)₂C(O)N(CH₃)₂; —NHCH(CH₂COOH)CO₂(CH₂)₃-morpholin-4-yl; —NHCH(CH₂COOH)CO₂(CH₂)₂OC(O)C(CH₃)₃; —NHCH(COOH)CH₂CO₂CH₃; —NHCH(CH₂COOH)CO₂(CH₂)₂N(CH₃)₂; —NHCH(COOH)CH₂CO₂CH₂C(O)N(CH₃)₂; —NHCH(CH₂COOH)CO₂CH₂C(O)N(CH₃)₂; —NHCH(CH₂COOH)CO₂CH₃; —NH(CH₂)₃N(CH₃)₂; —NHCH₂CH₂CO₂CH₃; —NHCH[CH₂CO₂CH₂C(O)N(CH₃)₂]—CO₂CH₂—C(O)—N(CH₃)₂; —NHCH₂CO₂CH₃; —N-(methyl 3-amino-3-deoxyaminopyranoside); —N-(methyl 3-amino-2,3,6-trideoxyhexopyranoside); —N-(2-amino-2-deoxy-6-(dihydrogenphosphate)-glucopyranose; —N-(2-amino-2-deoxygluconic acid); —NH(CH₂)₄COOH; —N—(N—CH₃-D-glucamine; —NH(CH₂)₆COOH; —O(D-glucose); —NH(CH₂)₃OC(O)CH(NH₂)CH₃; —NH(CH₂)₄CH(C(O)-2-HOOC-pyrrolidin-1-yl)NHCH(COOH)—CH₂CH₂Ph (S,S isomer); —NH—CH₂CH₂—NH—(CH₂)₉CH₃; or —NH(CH₂)C(O)CH₂C(O)N(CH₃)₂;

Preferably, R⁴, R⁶ and R⁷ are each independently selected from hydrogen or —C(O)R$^d$. More preferably, R⁴, R⁶ and R⁷ are each hydrogen.

Preferably $R^5$ is hydrogen, —$CH_2$—$NHR^c$, —$CH_2$—$NR^cR^e$ or —$CH_2$—NH—$R^a$—Y—$R^b$—$(Z)_x$. $R^5$ can also preferably be hydrogen; —$CH_2$—N—(N—$CH_3$—D-glucamine); —$CH_2$—NH—$CH_2CH_2$—NH—$(CH_2)_9CH_3$; —$CH_2$—NH—$CH_2CH_2$—NHC(O)—$(CH_2)_3COOH$; —$CH_2$—NH—$(CH_2)_9CH_3$; —$CH_2$—NH—$CH_2CH_2$—COOH; —$CH_2$—NH—$(CH_2)_5COOH$; —$CH_2$-(morpholin-4-yl); —$CH_2$—NH—$CH_2CH_2$—O—$CH_2CH_2OH$; —$CH_2$—NH—$CH_2CH(OH)$—$CH_2OH$; —$CH_2$—N[$CH_2CH_2OH$]$_2$; —$CH_2$—NH—$(CH_2)_3$—N$(CH_3)_2$; —$CH_2$—N[$(CH_2)_3$—N$(CH_3)_2$]$_2$; —$CH_2$—NH—$(CH_2)_3$-(imidazol-1-yl); —$CH_2$—NH—$(CH_2)_3$-(morpholin-4-yl); —$CH_2$—NH—$(CH_2)_4$—NHC(NH)$NH_2$; —$CH_2$—N-(2-amino-2-deoxygluconic acid); —$CH_2$—NH—$CH_2CH_2$—NH—$(CH_2)_{11}CH_3$; —$CH_2$—NH—CH(COOH)$CH_2COOH$; —$CH_2$—NH—$CH_2CH_2$—$NHSO_2$—$(CH_2)_7CH_3$; —$CH_2$—NH—$CH_2CH_2$—$NHSO_2$—$(CH_2)_8CH_3$; —$CH_2$—NH—$CH_2CH_2$—$NHSO_2$—$(CH_2)_9CH_3$; —$CH_2$—NH—$CH_2CH_2$—$NHSO_2$—$(CH_2)_{11}CH_3$; —$CH_2$—NH—$CH_2CH_2$—NH—$(CH_2)_7CH_3$; —$CH_2$—NH—$CH_2CH_2$—O—$CH_2CH_2OH$; —$CH_2$—NH—$CH_2CH_2C(O)$—N—(D-glucosamine); —$CH_2$—NH-(6-oxo-[1,3]oxazinan-3-yl); —$CH_2$—NH—$CH_2CH_2$—S—$(CH_2)_7CH_3$; —$CH_2$—NH—$CH_2CH_2$—S—$(CH_2)_8CH_3$; —$CH_2$—NH—$CH_2CH_2$—S—$(CH_2)_9CH_3$; —$CH_2$—NH—$CH_2CH_2$—S—$(CH_2)_{11}CH_3$; —$CH_2$—NH—$CH_2CH_2$—S—$(CH_2)_6Ph$; —$CH_2$—NH—$CH_2CH_2$—S—$(CH_2)_8Ph$; —$CH_2$—NH—$CH_2CH_2$—S—$(CH_2)_{10}Ph$; —$CH_2$—NH—$CH_2CH_2$—S—$CH_2$-(4-(4-$CF_3$-Ph)Ph); —$CH_2$—NH—$CH_2CH_2$—NH—$(CH_2)_{11}CH_3$; or —$CH_2$—NH—$(CH_2)_5$—COOH.

Preferably, $R^8$ is —$CH_2C(O)NH_2$, —$CH_2COOH$, benzyl, 4-hydroxyphenyl or 3-chloro-4-hydroxyphenyl.

Preferably, $R^9$ is hydrogen or alkyl.

Preferably, $R^{10}$ is alkyl or substituted alkyl. More preferably, $R^{10}$ is the side-chain of a naturally occurring amino acid, such as isobutyl.

Preferably, $R^{10}$ is hydrogen or alkyl.

Preferably, $R^{12}$ is hydrogen, alkyl, substituted alkyl or —C(O)$R^d$. $R^{12}$ can also preferably be hydrogen; —$CH_2COOH$; —$CH_2$—[CH(OH)]$_5CH_2OH$; —$CH_2CH$(OH)$CH_2OH$; —$CH_2CH_2NH_2$; —$CH_2C(O)OCH_2CH_3$; —$CH_2$-(2-pyridyl); —$CH_2$—[CH(OH)]$_4COOH$; —$CH_2$-(3-carboxyphenyl); (R)—C(O)CH($NH_2$)$(CH_2)_4NH_2$; —C(O)Ph; —C(O)$CH_2$NHC(O)$CH_3$; E—$CH_2CH_2$—S—$(CH_2)_3$CH=CH$(CH_2)_4CH_3$; or —C(O)$CH_3$.

Preferably, $X^1$ and $X^2$ are each chloro.

Preferably, $X^3$ is hydrogen.

Preferably, each Y is independently selected from the group consisting of oxygen, sulfur, —S—S—, —$NR^c$—, —S(O)—, —$SO_2$—, —$NR^cC(O)$—, —$OSO_2$—, —OC(O)—, —$NR^cSO_2$—, —C(O)$NR^c$—, —C(O)O—, —$SO_2NR^c$—, —$SO_2O$—, —P(O)(O$R^c$)O—, —P(O)(O$R^c$)$NR^c$—, —OP(O)(O$R^c$)O—, —OP(O)(O$R^c$)$NR^c$—, —OC(O)O—, —$NR^cC(O)O$—, —$NR^cC(O)NR^c$—, —OC(O)$NR^c$— and —$NR^cSO_2NR^c$—.

Preferably, n is 0 or 1, and more preferably, n is 1.

Preferably, the saccharide-amine is alkylated with an aldehyde of the formula W—CHO wherein W is selected from —$R^a$—Y—$R^b$—$(Z)_x$, alkyl, substituted alkyl, alkenyl, substituted alkenyl, alkynyl, substituted alkynyl, cycloalkyl, substituted cycloalkyl, cycloalkenyl, and substituted cycloalkenyl.

Preferably, the alkylated glycopeptide product is a compound of formula I wherein $R^1$ is an amino saccharide wherein the saccharide-amine is substituted with —$R^a$—Y—$R^b$—$(Z)_x$, alkyl, substituted alkyl, alkenyl, substituted alkenyl, alkynyl, substituted alkynyl, cycloalkyl, substituted cycloalkyl, cycloalkenyl, or substituted cycloalkenyl.

More preferably, the alkylated glycopeptide product is a compound of formula I wherein $R^1$ is an amino saccharide wherein the saccharide-amine is substituted with: —$CH_2CH_2$—NH—$(CH_2)_9CH_3$; —$CH_2CH_2CH_2$—NH—$(CH_2)_8CH_3$; —$CH_2CH_2CH_2CH_2$—NH—$(CH_2)_7CH_3$; —$CH_2CH_2$—$NHSO_2$—$(CH_2)_9CH_3$; —$CH_2CH_2$—$NHSO_2$—$(CH_2)_{11}$, $CH_3$; —$CH_2CH_2$—S—$(CH_2)_8CH_3$; —$CH_2CH_2$—S—$(CH_2)_9CH_3$; —$CH_2CH_2$—S—$(CH_2)_{10}CH_3$; —$CH_2CH_2CH_2$—S—$(CH_2)_8$ $CH_3$; —$CH_2CH_2CH_2$—S—$(CH_2)_9CH_3$; —$CH_2CH_2CH_2$—S—$(CH_2)_3$—CH=CH—$(CH_2)_4CH_3$ (trans); —$CH_2CH_2CH_2CH_2$—S—$(CH_2)_7CH_3$; —$CH_2CH_2$—S(O)—$(CH_2)_9CH_3$; —$CH_2CH_2$—S—$(CH_2)_6$Ph; —$CH_2CH_2$—S—$(CH_2)_8$Ph; —$CH_2CH_2CH_2$—S—$(CH_2)_8$ Ph; —$CH_2CH_2$—NH—$CH_2$-4-(4-Cl-Ph)-Ph; —$CH_2CH_2$—NH—$CH_2$-4-[4—$(CH_3)_2$CHCH$_2$—]-Ph; —$CH_2CH_2$—NH—$CH_2$-4-(4-$CF_3$-Ph)-Ph; —$CH_2CH_2$—S—$CH_2$-4-(4-Cl-Ph)-Ph; —$CH_2CH_2$—S(O)—$CH_2$-4-(4-Cl-Ph)-Ph; —$CH_2CH_2CH_2$—S—$CH_2$-4-(4-Cl-Ph)-Ph; —$CH_2CH_2CH_2$—S(O)—$CH_2$-4-(4-Cl-Ph)-Ph; —$CH_2CH_2CH_2$—S—$CH_2$-4-[3,4-di-Cl-PhCH$_2$O—)-Ph; —$CH_2CH_2$—$NHSO_2$—$CH_2$—-4-[4-(4-Ph)-Ph]-Ph; —$CH_2CH_2CH_2$—$NHSO_2$—$CH_2$-4-(4-Cl-Ph)-Ph; —$CH_2CH_2CH_2$—$NHSO_2$—$CH_2$-4-(Ph-C≡C—)-Ph; —$CH_2CH_2CH_2$—$NHSO_2$-4-(4-Cl-Ph)-Ph; or —$CH_2CH_2CH_2$—$NHSO_2$-4-(naphth-2-yl)-Ph. More preferably, the alkylated glycopeptide product is also compound of formula I wherein $R^1$ is an amino saccharide wherein the saccharide-amine is substituted with 4-(4-chlorophenyl)benzyl or 4-(4-chlorobenzyloxy)benzyl.

Preferably, the alkylated glycopeptide product is a compound of formula I wherein $R^1$ is a saccharide group of formula III, wherein $R^{15}$ is —$R^a$—$Y$—$(Z)_x$, alkyl, substituted alkyl, alkenyl, substituted alkenyl, alkynyl, substituted alkynyl, cycloalkyl, substituted cycloalkyl, cycloalkenyl, substituted cycloalkenyl. More preferably, $R^{15}$ is alkyl, substituted alkyl, alkenyl, substituted alkenyl, alkynyl, substituted alkynyl, cycloalkyl, substituted cycloalkyl, cycloalkenyl, or substituted cycloalkenyl.

More preferably, the alkylated glycopeptide product is a compound of formula I wherein $R^1$ is an amino saccharide of formula III, wherein $R^{15}$ is —$CH_2CH_2$—NH—$(CH_2)_9CH_3$; —$CH_2CH_2CH_2$—NH—$(CH_2)_8CH_3$; —$CH_2CH_2CH_2CH_2$—NH—$(CH_2)_7CH_3$; —$CH_2CH_2$—$NHSO_2$—$(CH_2)_9CH_3$; —$CH_2CH_2$—$NHSO_2$—$(CH_2)_{11}$ $CH_3$; —$CH_2CH_2$—S—$(C_2)_8CH_3$; —$CH_2CH_2$—S—$(CH_2)_9CH_3$; —$CH_2CH_2$—S—$(CH_2)_{10}CH_3$; —$CH_2CH_2CH_2$—S—$(CH_2)_8$ $CH_3$; —$CH_2CH_2CH_2$—S—$(CH_2)_9CH_3$; —$CH_2CH_2CH_2$—S—$(CH_2)_3$—CH=CH—$(CH_2)_4CH_3$ (trans); —$CH_2CH_2CH_2CH_2$—S—$(CH_2)_7CH_3$; —$CH_2CH_2$—S(O)—$(CH_2)_9CH_3$; —$CH_2CH_2$—S—$(CH_2)_6$Ph; —$CH_2CH_2$—S—$(CH_2)_8$Ph; —$CH_2CH_2CH_2$—S—$(CH_2)_8$Ph; —$CH_2CH_2$—NH—$CH_2$-4-(4-Cl-Ph)-Ph; —$CH_2CH_2$—NH—$CH_2$-4-[4—$(CH_3)_2$CHCH$_2$—]-Ph; —$CH_2CH_2$—NH—$CH_2$-4-(4$CF_3$-Ph)-Ph; —$CH_2CH_2$—S—$CH_2$-4-(4-Cl-Ph)-Ph; —$CH_2CH_2$—S(O)—$CH_2$-4-(4-Cl-Ph)-Ph; —$CH_2CH_2CH_2$—S—$CH_2$-4-(4-Cl-Ph)-Ph; —$CH_2CH_2CH_2$—S(O)—$CH_2$-4-(4-Cl-Ph)-Ph; —$CH_2CH_2CH_2$—S—$CH_2$-4-[3,4-di-Cl-PhCH$_2$O—)-Ph; —$CH_2CH_2$—$NHSO_2$—$CH_2$-4-[4-(4-Ph)-Ph]-Ph; —$CH_2CH_2CH_2$—$NHSO_2$—$CH_2$-4-(4-Cl-Ph)-Ph; —$CH_2CH_2CH_2$—$NHSO_2$—$CH_2$-4-(Ph-C≡C—)-Ph; —$CH_2CH_2CH_2$—$NHSO_2$-4-(4-Cl-Ph)-Ph; or —$CH_2CH_2CH_2$—$NHSO_2$-4-(naphth-2-yl)-Ph. More preferably $R^{15}$ can also be 4-(4-chlorophenyl)benzyl or 4-(4-chlorobenzyloxy)benzyl.

More preferably, the present invention provides a method for preparing an alkylated glycopeptide comprising: combining an aldehyde or ketone, a suitable base, and a compound of formula II:

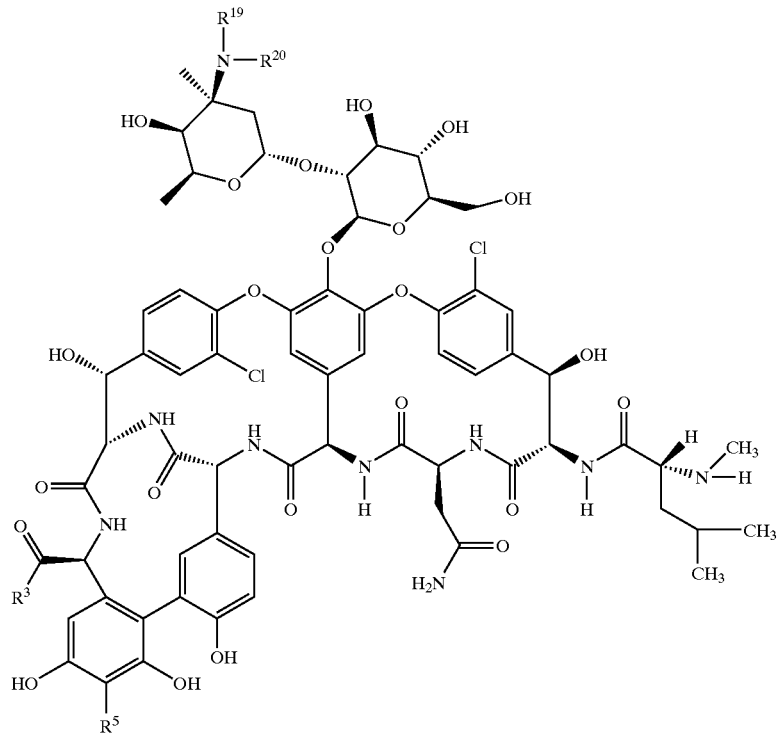

(II)

wherein:
R$^{19}$ and R$^{20}$ are each hydrogen; and R$^3$, and R$^5$ have any of the values or preferred values described herein; or a stereoisomer thereof; to provide a reaction mixture;
acidifying the reaction mixture; and
combining the reaction mixture with a suitable reducing agent, to provide the corresponding alkylated glycopeptide wherein R$^{20}$ is —R$^a$—Y—R$^b$—(Z)$_x$, alkyl, substituted alkyl, alkenyl, substituted alkenyl, alkynyl, substituted alkynyl, cycloalkyl, substituted cycloalkyl, cycloalkenyl, or substituted cycloalkenyl. Preferably, R$^{20}$ is alkyl, substituted alkyl, alkenyl, substituted alkenyl, alkynyl, substituted alkynyl, cycloalkyl, substituted cycloalkyl, cycloalkenyl, or substituted cycloalkenyl.

More preferably, the alkylated glycopeptide product is a compound of formula II wherein R$^{20}$ is —CH$_2$CH$_2$—NH—(CH$_2$)$_9$CH$_3$; —CH$_2$CH$_2$CH$_2$—NH—(CH$_2$)$_8$CH$_3$; —CH$_2$CH$_2$CH$_2$CH$_2$—NH—(CH$_2$)$_7$CH$_3$; —CH$_2$CH$_2$—NHSO$_2$—(CH$_2$)$_9$CH$_3$; —CH$_2$CH$_2$—NHSO$_2$—(CH$_2$)$_{11}$CH$_3$; —CH$_2$CH$_2$—S—(CH$_2$)$_8$CH$_3$; —CH$_2$CH$_2$—S—(CH$_2$)$_9$CH$_3$; —CH$_2$CH$_2$—S—(CH$_2$)$_{10}$CH$_3$; —CH$_2$CH$_2$CH$_2$—S—(CH$_2$)$_8$CH$_3$; —CH$_2$CH$_2$CH$_2$—S—(CH$_2$)$_9$CH$_3$; —CH$_2$CH$_2$CH$_2$—S—(CH$_2$)$_3$—CH=CH—(CH$_2$)$_4$CH$_3$ (trans); —CH$_2$CH$_2$CH$_2$CH$_2$—S—(CH$_2$)$_7$CH$_3$; —CH$_2$CH$_2$—S(O)—(CH$_2$)$_9$CH$_3$; —CH$_2$CH$_2$—S—(CH$_2$)$_6$Ph; —CH$_2$CH$_2$—S—(CH$_2$)$_8$Ph; —CH$_2$CH$_2$CH$_2$—S—(CH$_2$)$_8$Ph; —CH$_2$CH$_2$—NH—CH$_2$-4-(4-Cl-Ph)-Ph; —CH$_2$CH$_2$—NH—CH$_2$-4-[4-(CH$_3$)$_2$CHCH$_2$—]-Ph; —CH$_2$CH$_2$—NH—CH$_2$-4-(4-CF$_3$-Ph)-Ph; —CH$_2$CH$_2$—S—CH$_2$-4-(4-Cl-Ph)-Ph; —CH$_2$CH$_2$—S(O)—CH$_2$-4-(4-Cl-Ph)-Ph; —CH$_2$CH$_2$CH$_2$—S—CH$_2$-4-(4-Cl-Ph)-Ph; —CH$_2$CH$_2$CH$_2$—S(O)—CH$_2$-4-(4-Cl-Ph)-Ph; —CH$_2$CH$_2$CH$_2$—S—CH$_2$-4-[3,4-di-Cl-PhCH$_2$O—)-Ph; —CH$_2$CH$_2$—NHSO$_2$—CH$_2$-4-[4-(4-Ph)-Ph]-Ph; —CH$_2$CH$_2$CH$_2$—NHSO$_2$—CH$_2$-4-(4-Cl-Ph)-Ph; —CH$_2$CH$_2$CH$_2$—NHSO$_2$—CH$_2$-4-(Ph-C≡C—)-Ph; —CH$_2$CH$_2$CH$_2$—NHSO$_2$-4-(4-Cl-Ph)-Ph; or —CH$_2$CH$_2$CH$_2$—NHSO$_2$-4-(naphth-2-yl)-Ph. More preferably R$^{20}$ can also be 4-(4-chlorophenyl)benzyl or 4-(4-chlorobenzyloxy)benzyl.

A preferred aldehyde for use in the reductive alkylations is an aldehyde of formula: HC(=O)CH$_2$—NH—(CH$_2$)$_9$CH$_3$; HC(=O)CH$_2$CH$_2$—NH—(CH$_2$)$_8$CH$_3$; HC(=O)CH$_2$CH$_2$CH$_2$—NH—(CH$_2$)$_7$CH$_3$; HC(=O)CH$_2$—NHSO$_2$—(CH$_2$)$_9$CH$_3$; HC(=O)CH$_2$—NHSO$_2$—(CH$_2$)$_{11}$CH$_3$; HC(=O)CH$_2$—S—(CH$_2$)$_8$CH$_3$; HC(=O)CH$_2$—S—(CH$_2$)$_9$CH$_3$; HC(=O)CH$_2$—S—(CH$_2$)$_{10}$CH$_3$; HC(=O)CH$_2$CH$_2$—S—(CH$_2$)$_8$CH$_3$; HC(=O)CH$_2$CH$_2$—S—(CH$_2$)$_9$CH$_3$; HC(=O)CH$_2$CH$_2$—S—(CH$_2$)$_3$—CH=CH—(CH$_2$)$_4$CH$_3$ (trans); HC(=O)CH$_2$CH$_2$CH$_2$—S—(CH$_2$)$_7$CH$_3$; HC(=O)CH$_2$—S(O)—(CH$_2$)$_9$CH$_3$; HC(=O)CH$_2$—S—(CH$_2$)$_6$Ph; HC(=O)CH$_2$—S—(CH$_2$)$_8$ Ph; HC(=O)CH$_2$CH$_2$—S—(CH$_2$)$_8$Ph; HC(=O)CH$_2$—NH—HC(=O)—4—(4-Cl-Ph)-Ph; HC(=O)CH$_2$—NH—CH$_2$-4-[4-(CH$_3$)$_2$CHCH$_2$—]-Ph; HC(=O)CH$_2$—NH—CH$_2$-4-(4-CF$_3$-Ph)-Ph; HC(=O)CH$_2$—S—CH$_2$-4-(4-Cl-Ph)-Ph; HC(=O)CH$_2$—S(O)—CH$_2$-4-(4-Cl-Ph)-Ph; HC(=O)CH$_2$CH$_2$—S—CH$_2$-4-(4-Cl-Ph)-Ph; HC(=O)CH$_2$CH$_2$—S(O)—CH$_2$-4-(4-Cl-Ph)-Ph; HC(=O)CH$_2$CH$_2$—S—CH$_2$-4-[3,4-di-Cl-PhCH$_2$O—)-Ph; HC(=O)CH$_2$—NHSO$_2$—CH$_2$-4-[4-(4-Ph)-Ph; HC(=O)CH$_2$CH$_2$—NHSO$_2$—CH$_2$-4-(4-Cl-Ph)-Ph; HC(=O)CH$_2$CH$_2$—NHSO$_2$—CH$_2$-4-(Ph-C≡C—)-Ph; HC(=O)CH$_2$CH$_2$—NHSO$_2$-4-(4-Cl-Ph)-Ph; or HC(=O)CH$_2$CH$_2$—NHSO$_2$-4-(naphth-2-yl)-Ph.

The method of the invention is also particularly useful for preparing alkylated derivatives of the glycopeptide antibiotic A82846B (also known as chloroorienticin A or LY264826). See for example R. Nagarajan et al., *J. Org. Chem.,* 1988, 54, 983–986; and N. Tsuji et al., *J. Antibiot.,* 1988, 41, 819–822. The structure of this glycopeptide is similar to vancomycin, except A82846B contains an additional amino sugar (i.e. 4-epi-vancosamine attached at the $R^2$ position in formula I.) and further contains 4-epi-vancosamine in place of vancosamine in the disaccharide moiety attached at the $R^1$ position in formula I. The method of the invention is also particularly useful for preparing alkylated derivatives of the glycopeptide antibiotic A82846B that are substituted on the 4-epi-vancosamine nitrogen with a 4-(4-chlorophenyl)benzyl group or a 4-(4-chlorobenzyloxy)benzyl group.

The methods of the invention can also further comprise the step of removing a protecting group from the alkylated glycopeptide.

The methods of the invention can also further comprise, preparing a pharmaceutically acceptable salt of the alkylated glycopeptide. The methods of the invention can also further comprise, combining a pharmaceutically acceptable carrier with such a salt, to provide a pharmaceutical composition.

The methods of the invention can also further comprise, combining a pharmaceutically acceptable carrier with the alkylated glycopeptide, to provide a pharmaceutical composition.

DETAILED DESCRIPTION OF THE INVENTION

As used herein, the following terms have the following meanings, unless otherwise indicated.

Definitions

The term "alkyl" refers to a monoradical branched or unbranched saturated hydrocarbon chain preferably having from 1 to 40 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above, having from 1 to 8 substituents, preferably 1 to 5 substituents, and more preferably 1 to 3 substituents, selected from the group consisting of alkoxy, substituted alkoxy, cycloalkyl, substituted cycloalkenyl, cycloalkenyl, substituted cycloalkenyl, acyl, acylamino, acyloxy, amino, substituted amino, aminoacyl, aminoacyloxy, oxyaminoacyl, azido, cyano, guanido, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl —SO$_3$H, and —SO$_2$-heteroaryl.

The term "alkylene" refers to a diradical of a branched or unbranched saturated hydrocarbon chain, preferably having from 1 to 40 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group, as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. Preferably such fused groups contain from 1 to 3 fused ring structures. Additionally, the term substituted alkylene includes alkylene groups in which from 1 to 5 of the alkylene carbon atoms are replaced with oxygen, sulfur or —N— where R is hydrogen or alkyl. Examples of substituted alkylenes are chloromethylene (—CH(Cl)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$O—CH$_2$CH$_2$—) and the like.

The term "alkaryl" refers to the groups -alkylene-aryl and -substituted alkylene-aryl where alkylene, substituted alkylene and aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), n-propenyl (—CH$_2$CH=CH$_2$), iso-propenyl (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 40 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined above having from 1 to 5 substituents, preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon preferably having from 2 to 40 carbon atoms, more preferably 2 to 20 carbon atoms and even more preferably 2 to 6 carbon atoms and having at least 1 and preferably from 1–6 sites of acetylene (triple bond) unsaturation. Preferred alkynyl groups include ethynyl (—C≡CH), propargyl (—CH$_2$C≡CH) and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 40 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—CH$_2$C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, sulfonamide, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

"Amino acid" refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

The term "carboxy" refers to —COOH.

The term "C-terminus" as it relates to a glycopeptide is well understood in the art. For example, for a glycopeptide of formula I, the C-terminus is the position substituted by the group R$^3$.

The term "dicarboxy-substituted alkyl" refers to an alkyl group substituted with two carboxy groups. This term includes, by way of example, —CH$_2$(COOH)CH$_2$COOH and —CH$_2$(COOH)CH$_2$CH$_2$COOH.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl —SO$_2$-aryl and —SO$_2$-heteroaryl.

The term "halo" or "halogen" refers to fluoro, chloro, bromo and iodo. "Haloalkyl" refers to alkyl as defined herein substituted by 1–4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxy, carboxyalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroarylalkyl" refers to (heteroaryl)alkyl- where heteroaryl and alkyl are as defined herein. Representative examples include 2-pyridylmethyl and the like.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocylooxy, thiol, thioalkoxy, substituted thioalkoxy, aryl, aryloxy, heteroaryl, heteroaryloxy, heterocyclic, heterocylooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, oxo (=O), and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Another class of heterocyclics is known as "crown compounds" which refers to a specific class of heterocyclic compounds having one or more repeating units of the formula [—(CH$_2$—)$_a$A—] where a is equal to or greater than 2, and A at each separate occurrence can be O, N, S or P. Examples of crown compounds include, by way of example only, [—(CH$_2$)$_3$—NH—]$_3$, [—((CH$_2$)$_2$O)$_4$—((CH$_2$)$_2$—NH)$_2$] and the like. Typically such crown compounds can have from 4 to 10 heteroatoms and 8 to 40 carbon atoms.

The term "heterocylooxy" refers to the group heterocyclic-O—.

The term "thioheterocylooxy" refers to the group heterocyclic-S—.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "prodrug" is well understood in the art and includes compounds that are converted to pharmaceutically active compounds of the invention in a mammalian system. For example, see *Remington's Pharmaceutical Sciences,* 1980, vol. 16, Mack Publishing Company, Easton, Pa., 61 and 424.

The term "saccharide group" refers to an oxidized, reduced or substituted saccharide monoradical covalently attached to the glycopeptide or other compound via any atom of the saccharide moiety, preferably via the aglycone carbon atom. The term includes amino-containing saccharide groups. Representative saccharides include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. For the purposes of this definition, these saccharides are referenced using conventional three letter nomenclature and the saccharides can be either in their open or preferably in their pyranose form.

The term "amino-containing saccharide group" or "amino saccharide" refers to a saccharide group having an amino substituent. Representative amino-containing saccharides include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

The term "saccharide-amine" refers to the amine group of an amino saccharide.

The term "spiro-attached cycloalkyl group" refers to a cycloalkyl group attached to another ring via one carbon atom common to both rings.

The term "stereoisomer" as it relates to a given compound is well understood in the art, and refers to another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, *Morrison and Boyde Organic Chemistry,* 1983, 4th ed., Allyn and Bacon, Inc., Boston, Mass., page 123

The term "sulfonamide" refers to a group of the formula —SO$_2$NRR, where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

The term "thioether derivatives" when used to refer to the glycopeptide compounds of this invention includes thioethers (—S—), sulfoxides (—SO—) and sulfones (—SO$_2$—).

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Cyclodextrin" refers to cyclic molecules containing six or more α-D-glucopyranose units linked at the 1,4 positions by α linkages as in amylose. β-Cyclodextrin or cycloheptaamylose contains seven α-D-glucopyranose units. As used herein, the term "cyclodextrin" also includes cyclodextrin derivatives such as hydroxypropyl and sulfobutyl ether cyclodextrins. Such derivatives are described for example, in U.S. Pat. Nos. 4,727,064 and 5,376,645. One preferred cyclodextrin is hydroxypropyl β-cyclodextrin having a degree of substitution of from about 4.1–5.1 as measured by FTIR. Such a cyclodextrin is available from Cerestar (Hammond, Ind., USA) under the name Cavitron™ 82003.

"Glycopeptide" refers to oligopeptide antibiotics (e.g. heptapeptide antibiotics), characterized by a multi-ring peptide core optionally substituted with saccharide groups, such as vancomycin. Examples of glycopeptides included in this definition may be found in "Glycopeptides Classification, Occurrence, and Discovery", by Raymond C. Rao and Louise W. Crandall, ("Drugs and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in *J. Amer. Chem. Soc.,* 1996, 118, 13107–13108; *J. Amer. Chem. Soc.,* 1997, 119, 12041–12047; and *J. Amer. Chem. Soc.,* 1994, 116, 4573–4590. Representative glycopeptides include those identified as A477, A35512, A40926, A41030, A42867, A47934, A80407, A82846, A83850 ,A84575, AB-65, Actaplanin, Actinoidin, Ardacin, Avoparcin, Azureomycin, Balhimycin, Chloroorientiein, Chloropolysporin, Decaplanin, N-demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UK-69542, UK-7205 1, Vancomycin, and the like. The term "glycopeptide" as used herein is also intended to include the general class of peptides disclosed above wherein one or more sugar moieties are absent, provide the glycopeptide comprises at least one amino saccharide. Also within the scope of the invention are glycopeptides that have been further appended with additional saccharide residues, especially aminoglycosides, in a manner similar to vancosamnine.

"Vancomycin" refers to a glycopeptide antibiotic having the formula:

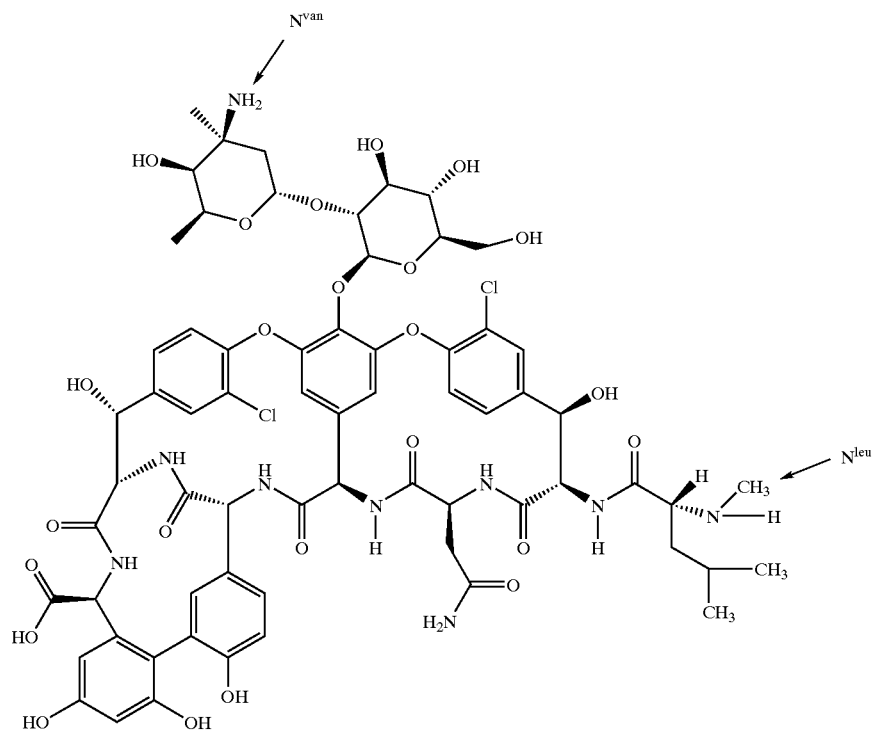

When describing vancomycin derivatives, the term "$N^{van}$-" indicates that a substituent is covalently attached to the amino group of the vacosamine moiety of vacomycin. Similarly, the term "$N^{leu}$-" indicates that a substituent is covalently attached to the amino group of the leucine moiety of vancomycin. The methods of the invention are particularly useful for selectively preparing $N^{van}$-alkylated derivatives over $N^{leu}$-alkylated derivatives.

"Optional" or "optionally" means that the subsequently described event or circumstance may or may not occur, and that the description includes instances where said event or circumstance occurs and instances in which it does not. For example, "optionally substituted" means that a group may or may not be substituted with the described substituent.

The term "nitrogen-linked" means a group or substituent is attached to the remainder of a compound (e.g. a compound of formula I) through a bond to a nitrogen of the group or substituent.

"Pharmaceutically acceptable salt" means those salts which retain the biological effectiveness and properties of the parent compounds and which are not biologically or otherwise harmful as the dosage administered. The compounds of this invention are capable of forming both acid and base salts by virtue of the presence of amino and carboxy groups respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of this invention typically contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

The term "protecting group" or "blocking group" refers to any group which, when bound to one or more hydroxyl, thiol, amino, carboxy or other groups of the compounds, prevents undesired reactions from occurring at these groups and which protecting group can be removed by conventional chemical or enzymatic steps to reestablish the hydroxyl, thio, amino, carboxy or other group. The particular removable blocking group employed is not critical and preferred removable hydroxyl blocking groups include conventional substituents such as alkyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" 3$^{rd}$ Ed., 1999, John Wiley and Sons, N.Y.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxy protecting groups include esters such as methyl, ethyl, propyl, t-butyl etc. which can be removed by mild conditions compatible with the nature of the product.

General Synthetic Procedures

As will be apparent to those skilled in the art, conventional protecting groups may be utilized to prevent certain functional groups from undergoing undesired reactions while carrying out the methods of the invention. The choice of a suitable protecting group for a particular functional group as well as suitable conditions for protection and deprotection are well known in the art. For example, numerous protecting groups, and their introduction and removal, are described in T. W. Greene and G. M. Wuts, *Protecting Groups in Organic Synthesis,* Third Edition, Wiley, New York, 1999, and references cited therein.

In the following reaction schemes, the glycopeptide compounds are depicted in a simplified form as a box "G" that shows the carboxy terminus labeled [C], the vancosamine amino terminus labeled [V], the "non-saccharide" amino terminus (i.e. the leucine amine moiety) labeled [N], and optionally, the resorcinol moiety labeled [R] as follows:

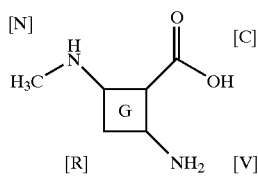

By way of illustration, a glycopeptide compound, such as vancomycin, can be reductive alkylated according to a method of the invention as illustrated in the following reaction:

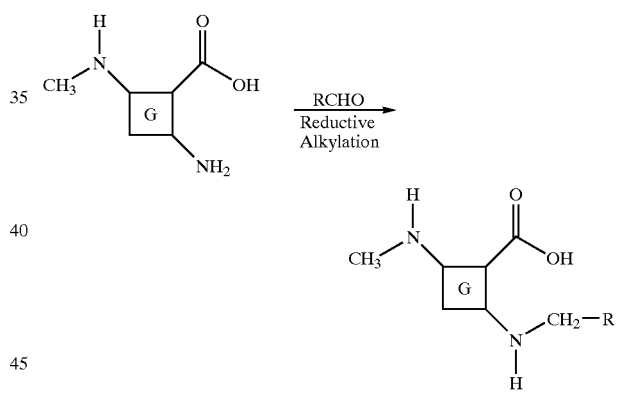

This reaction is typically conducted by first contacting one equivalent of the glycopeptide (e.g., vancomycin) with an excess, preferably, with about 1.1 to 3 equivalents, of an aldehyde (or ketone) in the presence of an excess, preferably about 1.1 about 3.5 equivalents, of a tertiary amine, such as diisopropylethylamine (DIPEA) or the like, to form an imine and/or hemiaminal intermediate or mixture of such intermediates. This reaction is typically conducted in an inert diluent, such as DMF or acetonitrile/water, at a temperature ranging from about 0° C. to about 50° C., preferably at ambient temperature, for about 0.25 to about 2 hours or until formation of the imine and/or hemiaminal intermediate(s) is substantially complete. The imine and/or hemiaminal intermediate(s) is typically not isolated, but is contacted in situ with an acid, such as trifluoroacetic acid, for a period of time sufficient to partially or completely hydrolyze any imine and/or hemiaminal formed at the N-terminus of the glycopeptide (e.g., at the leucinyl amino group of vancomycin). Typically, the reaction mixture containing the imine and/or hemiaminal intermediate(s) is contacted with an excess of the acid, preferably with about 1.2 to 8 equivalents, at a temperature ranging from about 0° C. to about 50° C., preferably at ambient temperature, for about 0.25 to about 6 hours; preferably, for about 0.5 to about 3 hours; more preferably, for about 1 to about 2 hours. A reducing agent, such as sodium cyanoborohydride, is then added to the reaction mixture to form the alkylated reaction product. Optionally, a protic solvent, such as methanol, is also added with the reducing agent. Typically, this reduction reaction is conducted by contacting the reaction mixture with at least one equivalent, preferably about 1.0 to about 3 equivalents, of the reducing agent at a temperature ranging from about 0° C. to about 50° C., preferably at ambient temperature, until the reduction reaction is substantially complete, preferably, for 0.1 to 6 hours; more preferably, for about 2 to 4 hours. The resulting alkylated product is readily purified by conventional procedures, such as precipitation and/or reverse-phase HPLC. Surprisingly, by forming the imine and/or hemiaminal in the presence of a trialkyl amine, and then acidifying with trifluoroacetic acid before contact with the reducing agent, the selectivity for the reductive alkylation reaction is greatly improved.

Additionally, ketones may substituted for the aldehydes in the reductive alkylation reactions to afford a-substituted amines.

Suitable starting materials for the methods of the invention, which are substituted at the resorcinol moiety [R], can be prepared as illustrated in the following scheme (in this scheme, the resorcinol moiety has been shown for clarity). For example, an aminoalkyl sidechain at the resorcinol moiety of a glycopeptide, such as vancomycin, can be introduced via a Mannich reaction. In this reaction, an amine (NHR$^c$R$^c$) and an aldehyde (CH$_2$O), such as formalin (a source of formaldehyde), are reacted with the glycopeptide under basic conditions to give the glycopeptide derivative:

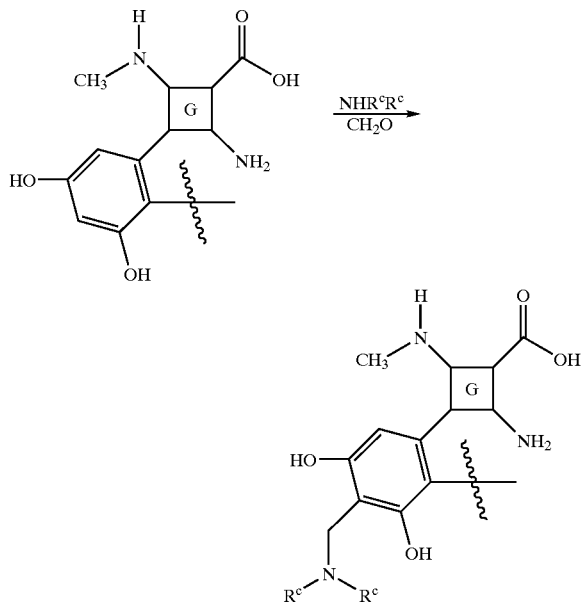

Accordingly, the methods of the invention can optionally comprise the step of first preparing a starting material that is substituted at the resorcinol moiety (e.g. using a procedure similar to that described above).

A substituent can also be introduced at the resorcinol moiety of a glycopeptide after carrying out the reductive alkylation of the invention. Accordingly, the method of the invention can also optionally further comprise alkylating the glycopeptide antibiotic that is alkylated at a saccharide-amine at the resorcinol moiety [R] (e.g. using a procedure similar to that described above), to provide a glycopeptide antibiotic that is alkylated at a saccharide-amine and that is substituted on the resorcinol ring.

The glycopeptide compounds can also be modified at the carboxy terminus either prior to or subsequent to the reductive alkylation to provide a glycopeptide antibiotic.

Compounds of the invention comprising a sulfoxide or sulfone can be prepared from the corresponding thio compounds using conventional reagents and procedures. Suitable reagents for oxidizing a thio compound to a sulfoxide include, by way of example, hydrogen peroxide, peracides such as 3-chloroperoxybenzoic acid (MCPBA), sodium periodate, sodium chlorite, sodium hypochlorite, calcium hypochlorite, tert-butyl hypochlorite and the like. Chiral oxidizing reagents, (optically active reagents) may also be employed to provide chiral sulfoxides. Such optically active reagents are well-known in the art and include, for example, the reagents described in Kagen et al., *Synlett.*, 1990, 643–650.

The aldehydes and ketones employed in the above reactive alkylation reactions are also well-known in the art and are either commercially available or can be prepared by conventional procedures using commercially available starting materials and conventional reagents (for example see March, *Advanced Organic Chemistry*, Fourth Edition, John Wiley & Sons, New York (1992), and references cited therein).

Pharmaceutical Compositions

A glycopeptide compound, preferably in the form of a pharmaceutically acceptable salt, can be formulated for oral or parenteral administration for the therapeutic or prophylactic treatment of bacterial infections.

By way of illustration, the glycopeptide compound can be admixed with conventional pharmaceutical carriers and excipients and used in the form of tablets, capsules, elixirs, suspensions, syrups, wafers, and the like. Such pharmaceutical compositions will contain from about 0.1 to about 90% by weight of the active compound, and more generally from about 10 to about 30%. The pharmaceutical compositions may contain common carriers and excipients, such as corn starch or gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The alkylated glycopeptide derivatives can be formulated in an aqueous solution containing a cyclodextrin. In another preferred embodiment the glycopeptide derivatives of this invention are formulated as a lyophilized powder containing a cyclodextrin or as a sterile powder containing a cyclodextrin. Preferably, the cyclodextrin is hydroxypropyl-β-cyclodextrin or sulfobutyl ether β-cyclodextrin; more preferably, the cyclodextrin is hydroxypropyl-β-cyclodextrin. Typically, in an injectable solution, the cyclodextrin will comprise about 1 to 25 weight percent; preferably, about 2 to 10 weight percent; more preferable, about 4 to 6 weight percent, of the formulation. Additionally, the weight ratio of the cyclodextrin to the alkylated glycopeptide derivative will preferably be from about 1:1 to about 10:1.

The alkylated glycopeptide derivatives that are active on rectal administration can be formulated as suppositories. A typical suppository formulation will generally consist of active ingredient with a binding and/or lubricating agent such as a gelatin or cocoa butter or other low melting vegetable or synthetic wax or fat.

The alkylated glycopeptide derivatives that are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991. Such patches may be constructed for continuous, pulsatile, or on demand delivery of pharmaceutical agents.

The following examples are offered to illustrate the invention and are not to be construed in any way as limiting the scope of this invention.

EXAMPLES

In the examples below, any abbreviations not defined have their generally accepted meaning. Unless otherwise stated, all temperatures are in degrees Celsius.

Vancomycin hydrochloride hydrate was purchased from Alpharma, Inc. Fort Lee, N.J. 07024 (Alpharma AS, Oslo Norway). Other reagents and reactants are available from Aldrich Chemical Co., Milwaukee, Wis. 53201.

Example 1

Reductive Alkylation of Vancomycin According to the Method of the Invention

Synthesis of a Compound of Formula II Wherein $R^3$ is —OH; $R^5$ is H; $R^{19}$ is H; and $R^{20}$ is $CH_3(CH_2)_9SCH_2CH_2$—

A solution of vancomycin hydrochloride (3.0 g, 2.1 mmol) in $ACN/H_2O$ (1:1, 30 mL) was treated with diisopropylethylamine (0.54 g, 0.72 mL, 4.2 mmol) followed by decylthioacetaldehyde (0.91 g, 4.2 mmol) at 25° C. After 30 minutes, the reaction solution was treated with trifluoroacetic acid (1.92g, 1.29 mL, 16.8 mmol) followed by sodium cyanoborohydride ($NaCNBH_3$, 0.132 g, 2.1 mmol). After 5–10 minutes, acetonitrile (300 mL) was added to provide the title compound as a white precipitate.

Example 2

Reductive Alkylation of Vancomycin According to the Method of the Invention

Synthesis of a Compound of Formula II Wherein $R^3$ is —OH; $R^5$ is H; $R^{19}$ is H; and $R^{20}$ is $CH_3(CH_2)_9SCH_2CH_2$—

Under nitrogen, to a solution of S-decyl mercaptoacetaldehyde (crude, 48 g, 220 mmol) in N,N-dimethylformamide (1.4 L) was added solid vancomycin hydrochloride hydrate (173 g, 100 mmol) followed by N,N-diisopropylethylamine (58 mL, 330 mmol). The suspension was stirred vigorously at room temperature for 2 hours, and all the vancomycin dissolved. Then, trifluoroacetic acid (53 mL, 690 mmol) was added. The solution was stirred an additional 90 minutes, then solid sodium cyanoborohydride (10.5 g, 170 mmol) followed by methanol (800 mL) were added. After three hours the reaction was analyzed by reverse-phase HPLC. The product distribution based on uv absorption at 280 nm was as follows.

| Elution time (min) | Area % | |
|---|---|---|
| 2.0 | 15 | Vancomycin |
| 3.2 | 77 | Title Compound |
| 3.3 | 3 | |
| 3.4 | 0.5 | Alkylation on N-methyl leucine |
| 4.0 | 0.8 | Alkylation on both vancosamine and N-methyl leucine |
| 4.1 | 0.4 | |

The reaction mixture was poured into water (7 L), resulting in a slightly cloudy solution. The pH of the solution was adjusted to 5 with saturated sodium bicarbonate, resulting in the formation of a white precipitate. This precipitate was collected by filtration, washed with water and then ethyl acetate, and dried under vacuum to provide the title compound.

Example 3

Comparative Example

Synthesis of a Compound of Formula II wherein $R^3$ is —OH; $R^5$ is H; $R^{19}$ is H; and $R^{20}$ is $CH_3(CH_2)_9SCH_2CH_2$—

Under nitrogen, vancomycin hydrochloride hydrate (1 g, 0.64 mmol) was added to S-decyl mercaptoacetaldehyde (139 mg, 0.64 mmol) in N,N-dimethylformamide (8mL). N,N-diisopropylethylamine (336 µL, 1.9 mmol) was added and the suspension stirred vigorously for 2.5 hours, over the course of which all the vancomycin dissolved. Solid sodium cyanoborohydride (60 mg, 0.96 mmol) was added, followed by methanol (5 mL) and trifluoroacetic acid (250 µL, 2.3 mmol). The reaction was stirred for 55 minutes at room temperature and analyzed by reverse phase HPLC. The product distribution based on uv absorption at 280 nm was as follows:

| Elution time (min) | Area % | |
|---|---|---|
| 2.0 | 29 | Vancomycin |
| 3.1 | 50 | Title Compound |
| 3.2 | 2 | |
| 3.3 | 7 | Alkylation on N-methyl leucine |
| 3.9 | 13 | Alkylation on both vancosamine and N-methyl leucine |
| 4.0 | 0.5 | |

Comparison of the HPLC data from Example 2 and Example 3 demonstrates that synthetic method of the invention (Example 2) provides a product mixture with a significantly higher percentage of the compound resulting from alkylation at the amino saccharide group, and a lower percentage of the compounds resulting from alkylation at the N-methyl leucine, or from bis alkylation (alkylation at both the amino saccharide group and at the N-methyl leucine).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in fall, as though individually incorporated by reference.

What is claimed is:

1. A method for alkylating a glycopeptide that comprises a saccharide-amine; the method comprising:
   (a) combining an aldehyde or ketone, a base, and the glycopeptide or a salt thereof, to provide a reaction mixture;
   (b) acidifying the reaction mixture; and
   (c) combining the reaction mixture with a reducing agent, to provide a glycopeptide that is alkylated at the saccharide-amine.

2. The method of claim 1 wherein the glycopeptide comprises at least one amino group other than the saccharide-amine.

3. The method of claim 2 wherein reductive alkylation at the saccharide-amine is favored over reductive alkylation at the other amino group of the glycopeptide by at least about 10:1.

4. The method of claim 2 wherein reductive alkylation at the saccharide-amine is favored over reductive alkylation at the other amino group of the glycopeptide by at least about 20:1.

5. The method of claim 1 wherein the reductive alkylation is carried out in the presence of a solvent.

6. The method of claim 5 wherein the solvent is a halogenated hydrocarbon, a linear or branched ether, an aromatic hydrocarbon, an alcohol, dimethylsulfoxide, N,N-dimethylformamide, acetonitrile, water, 1,3-dimethyl-3,4,5,6-tetrahydro-2(1H)-pyrimidone, tetramethyl urea, N,N-dimethylacetamide, diethylformamide, 1-methyl-2-pyrrolidinone, tetramethylenesulfoxide, glycerol, ethyl acetate, isopropyl acetate, N,N-dimethylpropylene urea, or dioxane, or a mixture thereof.

7. The method of claim 6 wherein the solvent is acetonitrile, water, N,N-dimethylformamide, or methanol, or mixtures thereof.

8. The method of claim 1 wherein the reaction mixture that is combined with the reducing agent comprises a protic solvent.

9. The method of claim 1 wherein the reductive alkylation is carried out at a temperature in a range of about 0° C. to about 50° C.

10. The method of claim 1 wherein the base is a tertiary amine.

11. The method of claim 1 wherein the reaction mixture is acidified with a carboxylic acid or a mineral acid.

12. The method of claim 1 wherein the reaction mixture is acidified with trifluoroacetic acid.

13. The method of claim 1 wherein the reducing agent is sodium cyanoborohydride, sodium triacetoxyborohydride, pyridine/borane, sodium borohydride, or zinc borohydride.

14. The method of claim 1 wherein the reducing agent is a hydrogen source and a transition metal catalyst.

15. A method for preparing an alkylated glycopeptide, the method comprising:
   (a) combining an aldehyde or ketone, a base, and a glycopeptide or a salt thereof, to provide a reaction mixture;
   (b) acidifying the reaction mixture;
   (c) combining the reaction mixture with a reducing agent to provide a glycopeptide that is alkylated at the saccharide-amine; and
   (d) isolating the alkylated glycopeptide.

16. A method for preparing an alkylated glycopeptide, the method comprising:
   (a) combining an aldehyde or ketone, a base, and a compound of formula I:

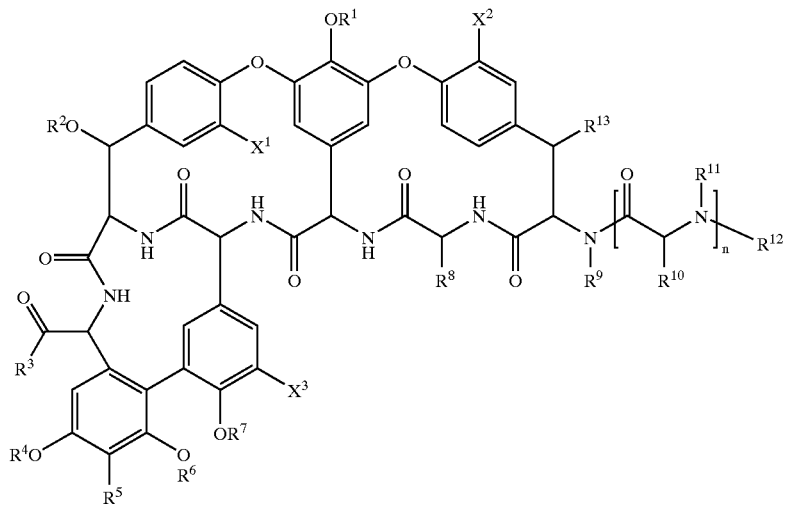

(I)

wherein:
R¹ is an amino saccharide group;
R² is hydrogen or a saccharide group;
R³ is —OR$^c$, —NR$^c$R$^c$, —O—R$^a$—Y—R$^b$—(Z)$_x$, —NR$^c$—R$^a$—Y—R$^b$—(Z)$_x$, —NR$^c$R$^c$, or —O—R$^c$;
R⁴ is selected from the group consisting of hydrogen, alkyl, substituted alkyl, alkenyl, substituted alkenyl, alkynyl, substituted alkynyl, —C(O)R$^d$ and a saccharide group;
R⁵ is selected from the group consisting of hydrogen, halo, —CH(R$^c$)—NR$^c$R$^c$, —CH(R$^c$)—NR$^c$R$^c$, —CH(R$^c$)—NR$^c$—R$^a$—Y—R$^b$—(Z)$_x$, —CH(R$^c$)—R$^x$, and —CH(R$^c$)—NR$^c$—R$^a$—C(=O)—R$^x$;
R⁶ is selected from the group consisting of hydrogen, alkyl, substituted alkyl, alkenyl, substituted alkenyl, alkynyl, substituted alkynyl, —C(O)R$^d$ and a saccharide group;
R⁷ is selected from the group consisting of hydrogen, alkyl, substituted alkyl, alkenyl, substituted alkenyl, alkynyl, substituted alkynyl, and —C(O)R$^d$;
R⁸ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;
R⁹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;
R¹⁰ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic; or R⁸ and R¹⁰ are joined to form —Ar¹—O—Ar²—, where Ar¹ and Ar² are independently arylene or heteroarylene;
R¹¹ is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic, or R¹⁰ and R¹¹ are joined, together with the carbon and nitrogen atoms to which they are attached, to form a heterocyclic ring;

R¹² is selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic, —C(O)R$^d$, —C(NH)R$^d$, —C(O)NR$^c$R$^c$, —C(O)OR$^d$, and —C(NH)NR$^c$R$^c$, or R¹¹ and R¹² are joined, together with the nitrogen atom to which they are attached, to form a heterocyclic ring;
R¹³ is selected from the group consisting of hydrogen or —OR¹⁴;
R¹⁴ is selected from hydrogen, —C(O)R$^d$ and a saccharide group;
each R$^a$ is independently selected from the group consisting of alkylene, substituted alkylene, alkenylene, substituted alkenylene, alkynylene and substituted alkynylene;
each R$^b$ is independently selected from the group consisting of a covalent bond, alkylene, substituted alkylene, alkenylene, substituted alkenylene, alkynylene and substituted alkynylene;
each R$^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —C(O)R$^d$;
each R$^d$ is independently selected from the group consisting of alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl and heterocyclic;
R$^e$ is a saccharide group;
R$^x$ is a nitrogen-linked amino saccharide or a nitrogen-linked heterocycle;
X¹, X² and X³ are independently selected from hydrogen or chloro;
each Y is independently selected from the group consisting of oxygen, sulfur, —S—S—, —NR$^c$—, —S(O)—, —SO₂—, —NR$^c$C(O)—, —OSO₂—, —OC(O)—, —NR$^c$SO₂—, —C(O)NR$^c$—, —C(O)O—, —SO₂NR$^c$—, —SO₂O—, —P(O)(OR$^c$)O—, —P(O)(OR$^c$)NR$^c$—, —OP(O)(OR$^c$)O—, —OP(O)

$(OR^c)NR^c$—, —OC(O)O—, —$NR^cC(O)O$—, —$NR^cC(O)NR^c$—, —$OC(O)NR^c$—, —C(=O)—, and —$NR^cSO_2NR_c$—, each Z is independently selected from hydrogen, aryl, cycloalkyl, cycloalkenyl, heteroaryl and heterocyclic;

n is 0, 1 or 2; and x is 1 or 2;

or a stereoisomer or salt thereof; to provide a reaction mixture;

(b) acidifying the reaction mixture; and (c) combining the reaction mixture with a reducing agent, to provide the corresponding glycopeptide alkylated at the amino group of the amino saccharide.

17. The method of claim 16 wherein $R^1$ is an amino saccharide of formula (III):

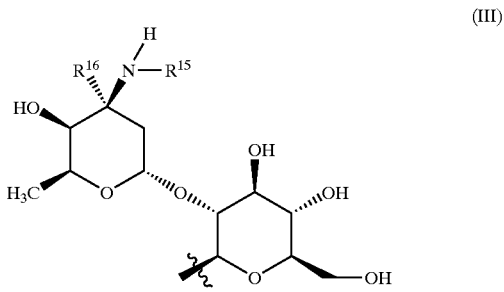

(III)

wherein $R^{15}$ is H; and $R^{16}$ is hydrogen or methyl.

18. The method of claim 16 wherein $R^2$, $R^4$, $R^6$, and $R^7$ are each hydrogen.

19. The method of claim 16 wherein $R^3$ is —OH.

20. The method of claim 16 wherein $R^5$ is hydrogen, —$CH_2$—$NHR^c$, —$CH_2$—$NR^cR^c$ or —$CH_2$—NR—$R^a$—Y—$R^b$—$(Z)_x$.

21. The method of claim 16 wherein the alkylated glycopeptide is a compound of formula I wherein $R^1$ is an amino saccharide wherein the saccharide-amine is substituted with —$R^a$—Y—$R^b$—$(Z)_x$, alkyl, substituted alkyl, alkenyl, substituted alkenyl, alkynyl, substituted alkynyl, cycloalkyl, substituted cycloalkyl, cycloalkenyl, or substituted cycloalkenyl.

22. The method of claim 16 wherein the alkylated glycopeptide is a compound of formula I wherein $R^1$ is an amino saccharide wherein the saccharide-amine is substituted with —$CH_2CH_2$—NH—$(CH_2)_9CH_3$; —$CH_2CH_2CH_2$—NH—$(CH_2)_8CH_3$; —$CH_2CH_2CH_2CH_2$—NH—$(CH_2)_7CH_3$; —$CH_2CH_2$—$NHSO_2$—$(CH_2)_9CH_3$; —$CH_2CH_2$—$NHSO_2$—$(CH_2)_{11}CH_3$; —$CH_2CH_2$—S—$(CH_2)_8CH_3$; —$CH_2CH_2$—S—$(CH_2)_9CH_3$; —$CH_2CH_2$—S—$(CH_2)_{10}CH_3$; —$CH_2CH_2CH_2$—S—$(CH_2)_8CH_3$; —$CH_2CH_2CH_2$—S—$(CH_2)_9CH_3$; —$CH_2CH_2CH_2$—S—$(CH_2)_3$—CH=CH—$(CH_2)_4CH_3$ (trans); —$CH_2CH_2CH_2CH_2$—S—$(CH_2)_7CH_3$; —$CH_2CH_2$—S(O)—$(CH_2)_9CH_3$; —$CH_2CH_2$—S—$(CH_2)_6Ph$; —$CH_2CH_2$—S—$(CH_2)_8Ph$; —$CH_2CH_2CH_2$—S—$(CH_2)_8Ph$; —$CH_2CH_2$—NH—$CH_2$-4-(4-Cl-Ph)-Ph; —$CH_2CH_2$—NH—$CH_2$-4-[4-$(CH_3)_2$CHCH$_2$—]-Ph; —$CH_2CH_2$—NH—$CH_2$-4-(4-CF$_3$-Ph)-Ph; —$CH_2CH_2$—S—$CH_2$-4-(4-Cl-Ph)-Ph; —$CH_2CH_2$—S(O)—$CH_2$-4-(4-Cl-Ph)-Ph; —$CH_2CH_2CH_2$—S—$CH_2$-4-(4-Cl-Ph)-Ph; —$CH_2CH_2CH_2$—S(O)—$CH_2$-4-(4-Cl-Ph)-Ph; —$CH_2CH_2CH_2$—S—$CH_2$-4-[3,4-di-Cl-PhCH$_2$O—)-Ph; —$CH_2CH_2$—$NHSO_2$—$CH_2$—4-[4-(4-Ph)-Ph]-Ph; —$CH_2CH_2CH_2$—$NHSO_2$—$CH_2$-4-(4-Cl-Ph)-Ph; —$CH_2CH_2CH_2$—$NHSO_2$—$CH_2$-4-(Ph-C≡C—)-Ph; —$CH_2CH_2CH_2$—$NHSO_2$-4-(4-Cl-Ph)-Ph; or —$CH_2CH_2CH_2$—$NHSO_2$-4-(naphth-2-yl)-Ph.

23. The method of claim 17 wherein the alkylated glycopeptide is a compound of formula I wherein $R^1$ is a saccharide group of formula III, wherein $R^{15}$ is —$R^a$—Y—$R^b$—$(Z)_x$, alkyl, substituted alkyl, alkenyl, substituted alkenyl, alkynyl, substituted alkynyl, cycloalkyl, substituted cycloalkyl, cycloalkenyl, substituted cycloalkenyl.

24. The method of claim 23 wherein $R^{15}$ is —$CH_2CH_2$—NH—$(CH_2)_9CH_3$; —$CH_2CH_2CH_2$—NH—$(CH_2)_8CH_3$; —$CH_2CH_2CH_2CH_2$—NH—$(CH_2)_7CH_3$; —$CH_2CH_2$—$NHSO_2$—$(CH_2)_9CH_3$; —$CH_2CH_2$—$NHSO_2$—$(CH_2)_{11}CH_3$; —$CH_2CH_2$—S—$(CH_2)_8CH_3$; —$CH_2CH_2$—S—$(CH_2)_9CH_3$; —$CH_2CH_2$—S—$(CH_2)_{10}CH_3$; —$CH_2CH_2CH_2$—S—$(CH_2)_8CH_3$; —$CH_2CH_2CH_2$—S—$(CH_2)_9CH_3$; —$CH_2CH_2CH_2$—S—$(CH_2)_3$—CH=CH—$(CH_2)_4CH_3$ (trans); —$CH_2CH_2CH_2CH_2$—S—$(CH_2)_7CH_3$; —$CH_2CH_2$—S(O)—$(CH_2)_9CH_3$; —$CH_2CH_2$—S—$(CH_2)_6Ph$; —$CH_2CH_2$—S—$(CH_2)_8Ph$; —$CH_2CH_2CH_2$—S—$(CH_2)_8Ph$; —$CH_2CH_2$—NH—$CH_2$-4-(4-Cl-Ph)-Ph; —$CH_2CH_2$—NH—$CH_2$-4-[4-$(CH_3)_2$CHCH$_2$—]-Ph; —$CH_2CH_2$—NH—$CH_2$-4-(4CF$_3$-Ph)-Ph; —$CH_2CH_2$—S—$CH_2$-4-(4-Cl-Ph)-Ph; —$CH_2CH_2$—S(O)—$CH_2$-4-(4-Cl-Ph)-Ph; —$CH_2CH_2CH_2$—S—$CH_2$-4-(4-Cl-Ph)-Ph; —$CH_2CH_2CH_2$—S(O)—$CH_2$-4-(4-Cl-Ph)-Ph; —$CH_2CH_2CH_2$—S—$CH_2$-4-[3,4-di-Cl-PhCH$_2$O—)-Ph; —$CH_2CH_2$—$NHSO_2$—$CH_2$-4-[4-(4-Ph)-Ph]-Ph; —$CH_2CH_2CH_2$—$NHSO_2$—$CH_2$-4-(4-Cl-Ph)-Ph; —$CH_2CH_2CH_2$—$NHSO_2$—$CH_2$-4-(Ph—C≡C—)-Ph; —$CH_2CH_2CH_2$—$NHSO_2$-4-(-4-Cl-Ph)-Ph; or —$CH_2CH_2CH_2$—$NHSO_2$-4-(naphth-2-yl)-Ph.

25. A method for preparing an alkylated glycopeptide, the method comprising:

(a) combining un aldehyde or ketone, a suitable base, and a compound of formula II:

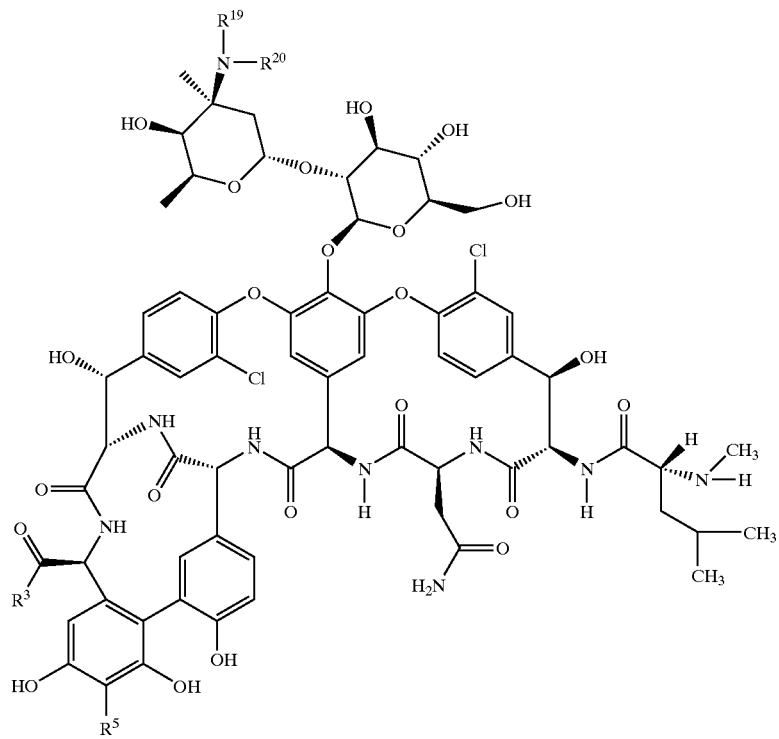

(II)

wherein:

$R^3$ is —$OR^c$, —$NR^cR^c$, —O—$R^a$—Y—$R^b$—$(Z)_x$, —$NR^c$—$R^a$—Y—$R^b$—$(Z)_x$, —$NR^cR^c$, or —O—$R^c$;

$R^5$ is selected from the group consisting of hydrogen, halo, —$CH(R^c)$—$NR^cR^c$, —$CH(R^c)$—$NR^cR^c$, and —$CH(R^c)$—$NR^cR^a$—Y—$R^b$—(Z);

$R^{19}$ and $R^{20}$ are each hydrogen;

each $R^a$ is independently selected from the group consisting of alkylene, substituted alkylene, alkenylene, substituted alkenylene, alkynylene and substituted alkynylene;

each $R^b$ is independently selected from the group consisting of a covalent bond, alkylene, substituted alkylene, alkenylene, substituted alkenylene, alkynylene and substituted alkynylene;

each $R^c$ is independently selected from the group consisting of hydrogen, alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, heterocyclic and —$C(O)R^d$;

$R^e$ is a saccharide group;

each Y is independently selected from the group consisting of oxygen, sulfur, —S—S—, —$NR^c$—, —S(O)—, —$SO_2$—, —$NR^cC(O)$—, —$OSO_2$—, OC(O)—, —$NR^cSO_2$—, —$C(O)NR^c$—, —C(O)O—, —$SO_2NR^c$—, —$SO_2O$—, —P(O)(O$R^c$)O—, —P(O)(O$R^c$)$NR^c$—, —OP(O)(O$R^c$)O—, —OP(O)(O$R^c$)$NR^c$—, —OC(O)O—, —$NR^cC(O)O$—, —$NR^cC(O)NR^c$—, —OC(O)$NR^c$— and —$NR^cSO_2NR_c$—, each Z is independently selected from hydrogen, aryl, cycloalkyl, cycloalkenyl, heteroaryl and heterocyclic; and x is 1 or 2; or a stereoisomer or salt thereof; to provide a reaction mixture;

(b) acidifying the reaction mixture; and (c) combining the reaction mixture with a reducing agent, to provide the corresponding alkylated glycopeptide wherein $R^{20}$ is —$R^a$—Y—$R^b$—$(Z)_x$, alkyl, substituted alkyl, alkenyl, substituted alkenyl, alkynyl, substituted alkynyl, cycloalkyl, substituted cycloalkyl, cycloalkenyl, or substituted cycloalkenyl.

26. The method of claim 25 wherein $R^{20}$ is —$CH_2CH_2$—NH—$(CH_2)_9CH_3$; —$CH_2CH_2CH_2$—NH—$(CH_2)_8CH_3$; —$CH_2CH_2CH_2CH_2$—NH—$(CH_2)_7CH_3$; —$CH_2CH_2$—$NHSO_2$—$(CH_2)_9CH_3$; —$CH_2CH_2$—$NHSO_2$—$(CH_2)_{11}CH_3$; —$CH_2CH_2$—S—$(CH_2)_8CH_3$; —$CH_2CH_2$—S—$(CH_2)_9CH_3$; —$CH_2CH_2$—S—$(CH_2)_{10}CH_3$; —$CH_2CH_2CH_2$—S—$(CH_2)_8CH_3$; —$CH_2CH_2CH_2$—S—$(CH_2)_9CH_3$; —$CH_2CH_2CH_2$—S—$(CH_2)_3$—CH=CH—$(CH_2)_4CH_3$ (trans); —$CH_2CH_2CH_2CH_2$—S—$(CH_2)_7CH_3$; —$CH_2CH_2$—S(O)—$(CH_2)_9CH_3$; —$CH_2CH_2$—S—$(CH_2)_6$Ph; —$CH_2CH_2$—S—$(CH_2)_8$Ph; —$CH_2CH_2CH_2$—S—$(CH_2)_8$Ph; —$CH_2CH_2$—NH—$CH_2$-4-(4-Cl-Ph)-Ph; —$CH_2CH_2$—NH—$CH_2$-4-[4-$(CH_3)_2$CHCH$_2$—]-Ph; —$CH_2CH_2$—NH—$CH_2$-4-(4-CF$_3$-Ph)-Ph; —$CH_2CH_2$—S—$CH_2$-4-(4-Cl-Ph)-Ph; —$CH_2CH_2$—S(O)—$CH_2$-4-(4-Cl-Ph)-Ph; —$CH_2CH_2CH_2$—S—$CH_2$-4-(4-Cl-Ph)-Ph; —$CH_2CH_2CH_2$—S(O)—$CH_2$-4-(4-Cl-Ph)-Ph; —$CH_2CH_2CH_2$—S—$CH_2$-4-[3,4-di-Cl-PhCH$_2$O—)-Ph; —$CH_2CH_2$—$NHSO_2$—$CH_2$-4-[4-(4-Ph)-Ph]-Ph; —$CH_2CH_2CH_2$—$NHSO_2$—$CH_2$-4-(4-Cl-Ph)-Ph; —$CH_2CH_2CH_2$—$NHSO_2$—$CH_2$-4-(Ph—C≡C—)-Ph; —$CH_2CH_2CH_2$—$NHSO_2$-4-(4-Cl-Ph)-Ph; or —$CH_2CH_2CH_2$—$NHSO_2$-4-(naphth-2-yl)-Ph.

27. The method of claim 1, further comprising preparing a pharmaceutically acceptable salt of the alkylated glycopeptide.

28. The method of claim 1, further comprising, combining a pharmaceutically acceptable carrier with the alkylated glycopeptide to provide a pharmaceutical composition.

29. The method of claim 27, further comprising, combining a pharmaceutically acceptable carrier with the salt, to provide a pharmaceutical composition.

30. A process for preparing an alkylated glycopeptide, the process comprising the steps of:
   (a) contacting a glycopeptide having a amino-containing saccharide group with an aldehyde or ketone in the presence of a tertiary amine to form a reaction mixture;
   (b) acidifying the reaction mixture from step (a) with an acid;
   (c) contacting the reaction mixture from step (b) with a reducing agent to form an alkylated glycopeptide.

31. The process of claim 30, wherein the glycopeptide is vancomycin or A82846B.

32. The process of claim 30, wherein the tertiary amine is diisopropylethylamine, N-methylmorpholine or triethylamine.

33. The process of claim 30, wherein the acid is trifluoroacetic acid.

34. The process of claim 30, wherein the reducing agent is sodium cyanoborohydride, sodium triacetoxyborohydride, pyridine/borane, sodium borohydride or zinc borohydride.

* * * * *

UNITED STATES PATENT AND TRADEMARK OFFICE
CERTIFICATE OF CORRECTION

PATENT NO. : 6,831,150 B2
DATED : December 14, 2004
INVENTOR(S) : Martin S. Linsell It is certified that error appears in the above-identified patent and that said Letters Patent is hereby corrected as shown below:

Column 29,
Line 28, replace "-NR$^c$R$^c$, or -O-R$^c$;" with -- -NR$^c$R$^e$, or -O-R$^e$; --; and
Line 34, replace "CH(R$^c$)-NR$^c$R$^c$," with -- CH(R$^c$)-NR$^c$R$^e$, --;

Column 30,
Line 57, replace "R$^c$ is a saccharide group;" with -- R$^e$ is a saccharide group; --;

Column 31,
Line 3, replace "-NR$^c$SO$_2$NR$_c$-," with -- -NR$^c$SO$_2$NR$^c$-, --; and
Line 47, replace "-CH$_2$-NR$^c$R$^c$ or -CH$_2$-NR-R$^a$-" with
-- -CH$_2$-NR$^c$R$^e$ or -CH$_2$-NH-R$^a$- --.

Column 32,
Line 67, replace "un aldehyde or ketone, a suitable base," with -- an aldehyde or ketone, a base, --.

Column 33,
Line 34, replace "-NR$^c$R$^c$, or -O-R$^c$;" with -- -NR$^c$R$^e$, or -O-R$^e$; --;
Line 36, replace "-CH(R$^c$)-NR$^c$R$^c$," with -- -CH(R$^c$)-NR$^c$R$^e$, --;
Line 37, replace "-CH(R$^c$)-NR$^c$R$^a$-Y-R$^b$-(Z);" with
-- -CH(R$^c$)-NR$^c$-R$^a$-Y-R$^b$-(Z); --;
Line 53, replace "R$^c$ is a saccharide group;" with -- R$^e$ is a saccharide group; --;
Line 57, replace "OC(O)-," with -- -OC(O)-, --; and
Line 62, replace "-NR$^c$SO$_2$NR$_c$-," with -- -NR$^c$SO$_2$NR$^c$-, --.

Signed and Sealed this

Seventh Day of June, 2005

JON W. DUDAS
*Director of the United States Patent and Trademark Office*